United States Patent [19]

Brownlee et al.

[11] 4,091,818
[45] May 30, 1978

[54] CARDIAC PACING APPARATUS WITH ELECTROMAGNETIC INTERFERENCE PROTECTION

[75] Inventors: Robert R. Brownlee, State College; G. Frank O. Tyers, Hershey, both of Pa.

[73] Assignee: Research Corporation, New York, N.Y.

[21] Appl. No.: 711,254

[22] Filed: Aug. 3, 1976

[51] Int. Cl.$^2$ .............................................. A61N 1/36
[52] U.S. Cl. ............................................ 128/419 PG
[58] Field of Search ................. 128/419 PG, 421, 422, 128/423

[56] References Cited

U.S. PATENT DOCUMENTS

| | | | |
|---|---|---|---|
| 3,678,937 | 7/1972 | Cole et al. | 128/419 PG |
| 3,881,493 | 5/1975 | Cannon | 128/491 PG |
| 3,903,897 | 9/1975 | Wollons et al. | 128/419 PG |
| 3,920,024 | 11/1975 | Bowers | 128/419 PG |
| 3,972,334 | 8/1976 | Wickham | 128/419 PG |

*Primary Examiner*—William E. Kamm
*Attorney, Agent, or Firm*—Cooper, Dunham, Clark, Griffin & Moran

[57] ABSTRACT

A cardiac pacing apparatus of the type having a first signal processing channel which functions in the demand mode is disclosed including a second signal processing channel for detecting electromagnetic interference and causing the pacing apparatus to revert to a safe operating rate in the presence of such interference. In a preferred embodiment, the second signal processing channel has an enhanced high-frequency response with respect to that of the first signal processing channel in order to optimize interference detection. The second channel may receive an input from either a conventional cardiac sensing and pacing electrode, or else a second electrode, remote from the heart, may be provided for interference detection. When electromagnetic interference is detected by the second signal processing channel, an override of the conventional demand pacer inhibit function occurs and the pacing apparatus is switched to a safe operating rate, which may be either an appropriate predetermined fixed rate or a rate-limited rate synchronous with the detected electromagnetic interference. In an alternate embodiment, the gain of the second signal processing channel is reduced with respect to that of the first channel, and the pacing apparatus is switched to a safe operating rate upon the detection of electromagnetic interference having an amplitude level above that of natural cardiac signals.

9 Claims, 6 Drawing Figures

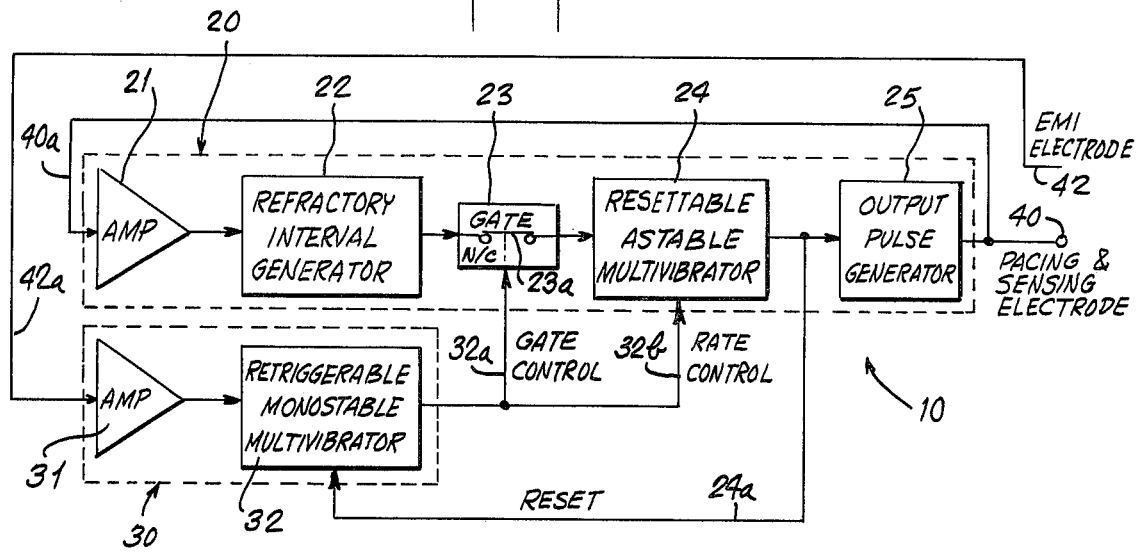
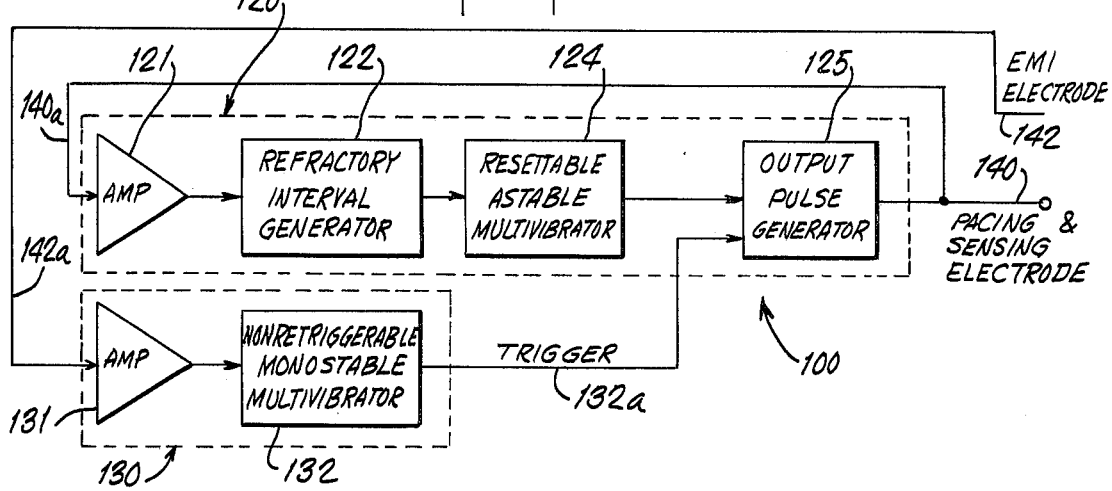
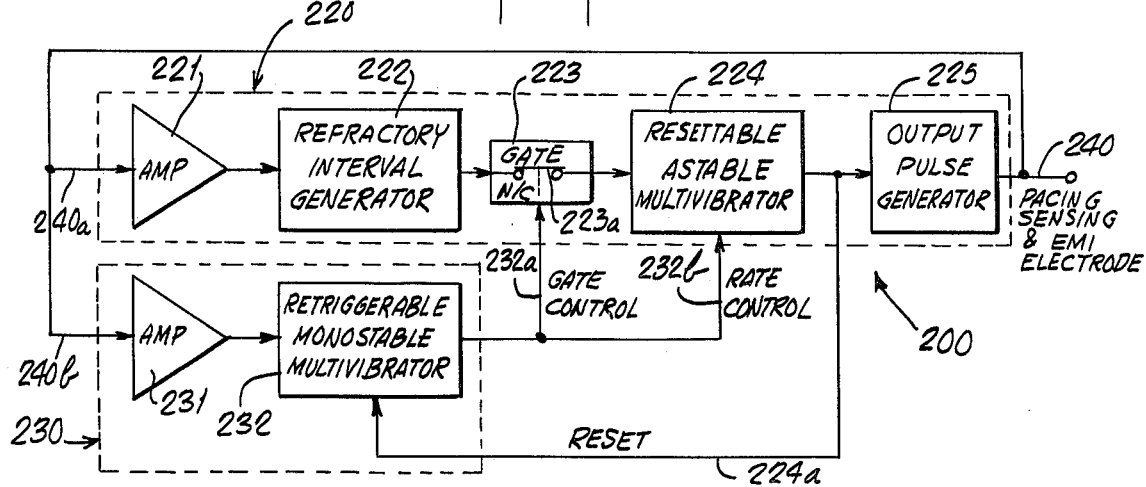

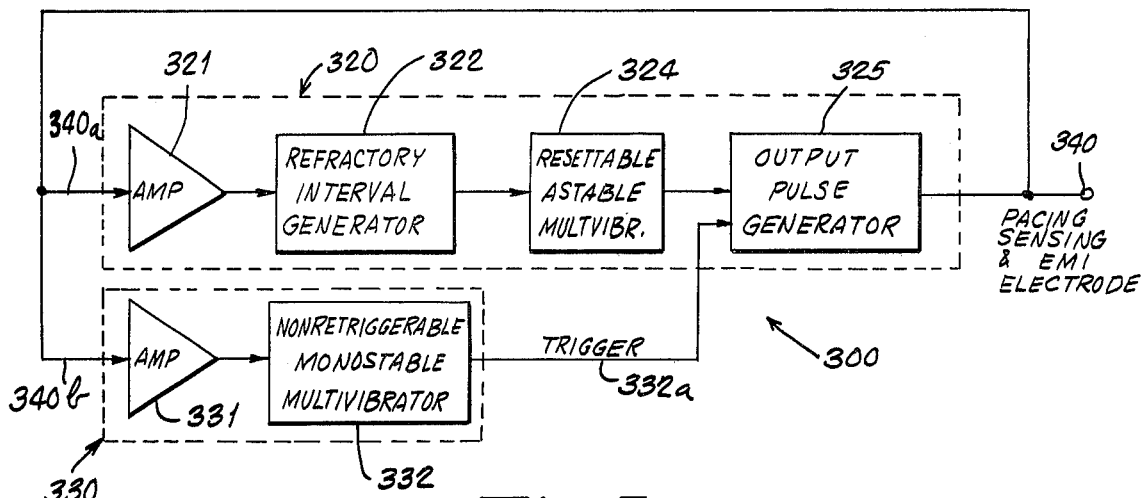
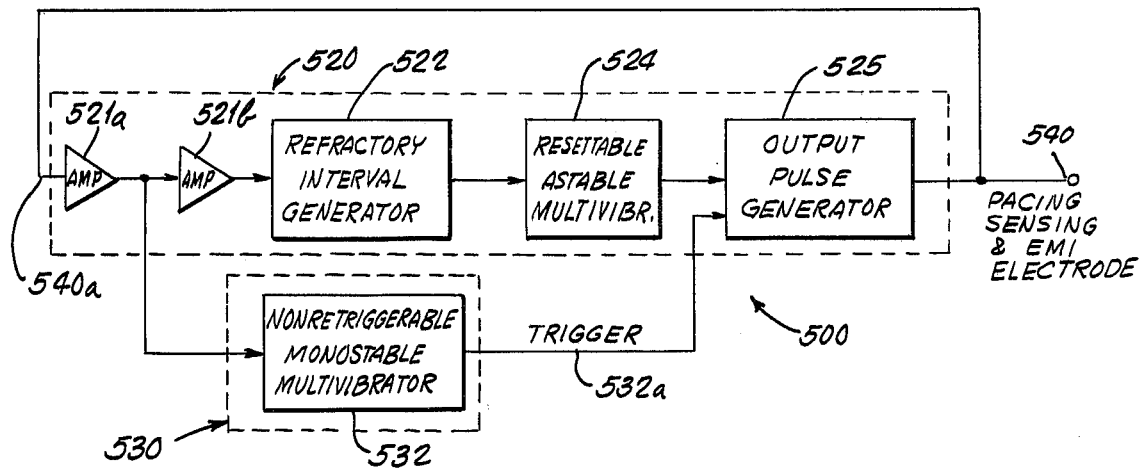
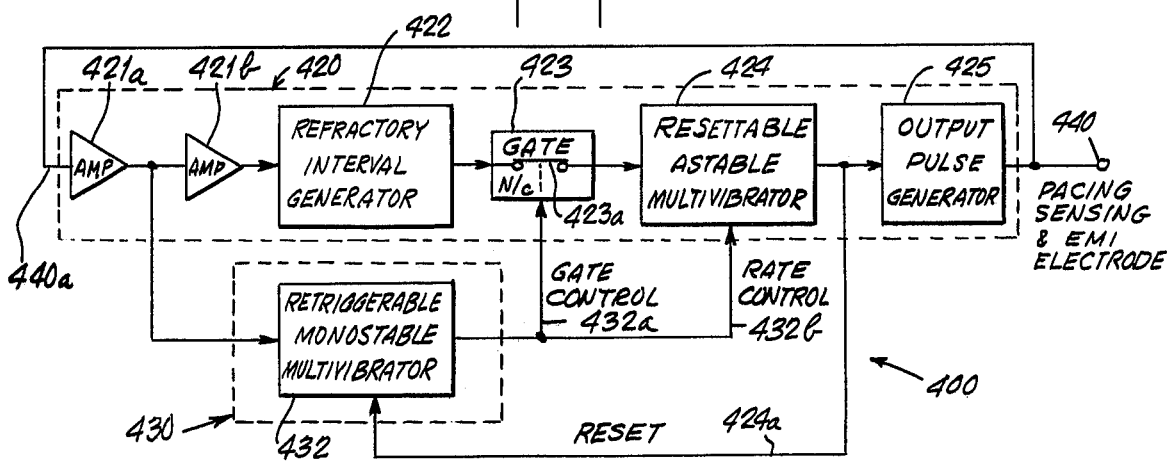

CARDIAC PACING APPARATUS WITH ELECTROMAGNETIC INTERFERENCE PROTECTION

BACKGROUND OF THE INVENTION

This invention relates to cardiac pacers and relates more particularly to pacers having enhanced electromagnetic interference (EMI) protection properties.

Programmed pacers may be functionally classified as either demand or synchronous devices. In the demand pacer, the generation of artificial cardiac pulses is inhibited during normal heart function, while in the synchronous pacer, artificial stimulating pulses synchronized with normal heart activity are generated. In the absence of cardiac activity, both types of pacers switch to a fixed rate mode and supply cardiac stimulating pulses at a predetermined fixed rate, typically in the order of about 70-80 pulses per minute.

Of the two basic programmed pacer types, the effect of electromagnetic interference is more severe in the demand pacer. This is because demand pacers are designed to deliver pacing pulses only when the natural heart rate falls below a predetermined minimum rate. This type of unit is therefore designed to shut off whenever the sensed heart rate (or any other detected input signal) is above the predetermined minimum rate. Accordingly, whenever an interference signal above this rate is detected, the demand pacer will be completely inhibited. If this phenomenon occurs during a period of cardiac malfunction that requires artificial pacing, the results may be fatal.

The consequences of electromagnetic interference detection in the synchronous configuration are somewhat less severe, and a synchronous pacer having enhanced performance in interference fields is disclosed in our prior U.S. Pat. No. 3,949,759.

The dangers associated with electromagnetic interference detection in demand pacers have been well documented, and although various partial solutions have been proposed, the performance of prior art demand pacers in certain types of interference fields has heretofore been unsatisfactory. Nevertheless, the demand pacer is preferred in many applications because it offers a substantial advantage over the synchronous pacer in the area of power consumption. Since the demand pacer does not generate artificial heart stimulating pulses when the patient's natural cardiac pacing and conduction systems are functioning properly (a condition which may exist in some patients for over 90% of the time), the use of a demand pacer rather than a synchronous device may result in substantially reduced battery drain.

Because of this substantial energy consumption advantage, considerable effort has been directed to overcoming the principal drawback of the demand pacer, namely its lack of safety in EMI fields. A typical prior art approach to the problem is shown in U.S. Pat. No. 3,877,438, in which a rate-sensitive interference rejection circuit is provided in a demand pacer. The function of this interference circuit, which is placed between the QRS detector and the pulse generator, is to prevent detected pulses from inhibiting the fixed-rate pulse generator if such pulses occur at too fast a rate. The detection of pulses at above a predetermined rate, which must necessarily be above the range of normal cardiac activity rates, is deemed to be an indication of detection of some kind of "noise", such as 60 Hz pickup, and the pacer is switched to its fixed-rate mode for so long as such noise is detected. The principal drawback of this type of prior art interference rejection scheme is that it is inherently ineffective in the presence of EMI fields which mimic or mock normal cardiac repetition rates. Numerous well-documented interference sources, including ignition systems, household appliances, power tools and medical support equipment, as well as an ever-growing list of new interference sources, such as microwave ovens with stirring devices and anti-theft devices, can all produce pulsed EMI outputs which may mimic the rates of normal heart activity. This mimic condition is particularly severe if the pulsed EMI amplitude is high enough to be demodulated by input defibrillator protection circuits or by amplifier saturation. Such interference sources may thus inhibit prior art demand pacers, in spite of the inclusion of conventional rate discrimination interference rejection circuits, with possibly fatal results. Furthermore, conventional filtering and shielding techniques have proven ineffective, since the amplitude of detected EMI may exceed normal cardiac signal levels by a ratio of over 10,000 to 1.

Various prior art systems and circuits for reducing the effect of EMI on demand pacers are shown in U.S. Pat. Nos. 3,866,616, 3,911,929, 3,926,197 and 3,927,677. However, none of the interference rejection schemes disclosed therein are capable of rejecting interference signals with repetition rates which closely mimic natural cardiac activity.

SUMMARY OF THE INVENTION

The present invention provides a cardiac pacing apparatus of the demand type which is not inhibited by electromagnetic interference signals with repetition rates which closely mimic natural cardiac rates. This is accomplished by providing a cardiac pacing apparatus having a first signal processing channel of the demand type with a second signal processing channel for detecting EMI and controlling the output of the first channel in the presence of detected interference.

More specifically, the second signal processing channel may include an amplifier having selected frequency response characteristics to ensure that any signal capable of inhibiting the basic demand function of the first signal processing channel will also activate the second signal processing channel. When the second signal processing channel is activated by an EMI detection, control circuitry in this channel switches the cardiac pacer to a safe mode. This safe mode may be either the normal fixed-rate mode of the demand channel, a second fixed rate mode at a higher rate than the normal fixed rate to minimize the possibility of competitive pacing, or a rate-limited mode synchronous with the detected EMI signal. The second signal processing channel may be provided with an input signal from either a conventional cardiac sensing and pacing electrode, or else the second channel may be provided with its own sensing electrode remote from the heart.

Since virtually all EMI signals contain a substantially different spectral content than that of natural cardiac signals before such signals are processed by pacer circuits, an effective EMI control system may be achieved by feeding EMI signals directly to the second signal processing channel, which is designed to detect such differences in spectral content. Significantly, even those EMI signals which closely mimic natural cardiac signatures in both amplitude and repetition rate will exhibit distinctive spectral characteristics from those of natural cardiac signatures, if the signals are examined before processing by conventional pacer circuitry eliminates the differences. The present invention therefore provides a means for distinguishing previously indistinguishable EMI signals, and for switching the pacer to a safe operating mode in the presence of such interference.

In an alternate embodiment of the invention, the second signal processing channel may be provided with an amplifier which is responsive to amplitude differences between natural cardiac signatures and many EMI signals. Since natural cardiac signals are typically in the amplitude range of from about 1-40 millivolts, and since many EMI sources, and particularly pulsed EMI sources, generate substantially higher signal levels at the pacer input, the second signal processing channel may be designed to be responsive only to EMI signals at levels above those of natural cardiac signals, and to switch the pacer to a safe operating mode in the presence of such high-level signals. Although this embodiment is not capable of distinguishing EMI signals within the amplitude range of normal cardiac signals, it is still capable of substantially improving demand pacer safety in the presence of many types of EMI, particularly since many low level EMI signals can be effectively filtered to prevent inhibition.

The invention may be more completely understood by reference to the following detailed description, to be read in conjunction with the accompanying drawings.

BRIEF DESCRIPTION OF THE DRAWINGS

FIG. 1 is a system block diagram of a dual-electrode, fixed-rate output cardiac pacing apparatus in accordance with the invention;

FIG. 2 is a system block diagram of a dual-electrode, synchronous output cardiac pacing apparatus;

FIGS. 3 and 4 are single-electrode embodiments of the cardiac pacers of FIGS. 1 and 2, respectively;

FIG. 5 is a system block diagram of a single-electrode, fixed-rate output cardiac pacing apparatus in accordance with an alternate embodiment of the invention; and FIG. 6 is a system block diagram of a single-electrode, rate-limited synchronous output cardiac pacing apparatus in accordance with an alternate embodiment of the invention.

DETAILED DESCRIPTION

Referring to FIG. 1 of the drawings, there is shown a dual-electrode cardiac pacing apparatus generally identified by the reference numeral 10. The pacing apparatus comprises a first signal processing channel 20 which includes the series-connected elements of a typical demand pacer, namely a bandpass amplifier 21, a refractory interval generator 22, a resettable astable multivibrator 24 and an output pulse generator 25. The foregoing portions of the first signal processing channel operate in a conventional manner and may comprise any one of a variety of suitable analog or digital circuit configurations, as will be familiar to one skilled in the art.

Inserted between refractory interval generator 22 and resettable astable multivibrator 24 is a gate 23, shown schematically in FIG. 1 as comprising a normally-closed switch 23a, which is activated by a gate control line 32a, in a manner to be described hereinafter.

When a gate switch 23a is in its normally-closed position, first channel 20 functions as a conventional demand pacer. Cardiac activity is sensed by a pacing and sensing electrode 40 at the cardiac site, and sensed input signals are provided to bandpass amplifier 21 by an input lead 40a. Amplifier 21, which may be of any conventional type suitable for detecting cardiac signatures, may typically have a bandpass of about 20 to about 200 Hz. This amplifier will, of course, also be responsive to EMI signals picked up by input lead 40a which have spectral components within the amplifier bandpass, a condition often ensured by input defibrillator circuit detection or amplifier saturation.

The output from amplifier 21, which may represent sensed cardiac activity, sensed EMI, or both, is used to trigger refractory interval generator 22, which is a conventional component of prior art demand pacers used to generate a refractory interval of about 250-300 milliseconds. The purpose of the refractory interval is to prevent multiple triggering, which may typically result from complex QRS signatures, after-potentials, elevated S-T segments or high-amplitude T waves. The refractory interval generator may be a nonretriggerable monostable multivibrator or any other suitable circuit.

When switch 23a is in its normally-closed position, the output of refractory interval generator 22 is fed directly to resettable astable multivibrator 24. Multivibrator 24, which may alternatively be any other suitable form of free-running pulse generator or a clocked resettable count-down circuit in a digital implementation, serves as a fixed-rate pulse generating circuit in the absence of an input signal. The natural rate of multivibrator 24, typically in the range of 70-80 pulses per minute, establishes the fixed rate of the demand pacer. An input signal received by multivibrator 24 from refractory interval generator 22 will cause the multivibrator to be reset without generating an output pulse. Thus, the demand channel so far described will serve as a fixed-rate pacer in the absence of detected cardiac or EMI signals, and will be inhibited in the presence of such signals. In the presence of continuous cardiac or pulsed EMI signals at or above the fixed rate, the fixed-rate mode will be continuously inhibited.

The output of multivibrator 24 triggers output pulse generator 25, which in turn generates an output pulse for application to the heart through electrode 40. The circuit parameters of output pulse generator 25 are selected to obtain a desired output amplitude, pulse width and output impedance in a manner well known to those skilled in the art. Output pulse generator 25 may typically be a monostable multivibrator, a resistance-capacitance coupled power driver, a transformer-coupled power driver, or any other suitable output circuit.

The cardiac pacing apparatus of FIG. 1 also includes an EMI detection electrode or antenna 42, which is located at a suitable nonactive site remote from the heart. This second EMI detection electrode may either be completely isolated from the pacing and sensing electrode 40, or else may be mounted on, but electrically insulated from, the pacing and sensing electrode lead-in to simplify the electrode-pacer interface.

Signals detected by EMI sensing electrode 42 are conducted by a lead 42a to a second signal processing channel 30. Second signal processing channel 30 includes a second bandpass amplifier 31, which produces a blocking signal when suitably activated, and a retriggerable monostable multivibrator 32 which is responsive to this blocking signal. The output of multivibrator 32 is coupled by gate control line 32a to gate 23, and by a rate control line 32b to multivibrator 24, while the output of multivibrator 24 is coupled by a reset line 24a to multivibrator 32. The basic purpose of the second signal processing channel 30, and the interconnections just described, is to detect the presence of EMI and to switch the first signal processing channel 20 to a safe, fixed-rate mode in the presence of such EMI, thereby defeating the normal inhibit function of the conventional demand pacer.

In order to ensure that any EMI signal which would inhibit the first channel is also detected by amplifier 31 of the second channel, this amplifier is provided with an enhanced high frequency response with respect to that of amplifier 21 of the first channel, and a midband gain which may equal or exceed that of the first channel amplifier. This configuration takes advantage of a significant but heretofore overlooked characteristic of many EMI signals which permits such signals to be distinguished from natural cardiac activity even when the interference is at normal cardiac repetition rates. One very common form of EMI, for example, is a pulsed RF signal consisting of repetitive damped sinusoidal waves with rapid rise time leading edges. Such interference may typically result from automotive ignition systems, electric motors, or the like, and may at times have a basic repetition rate which is indistinguishable from that of natural cardiac activity, i.e. in the range of from about 50 to 150 pulses per minute. Prior art demand pacers, even those of the type having rate-sensitive interference rejection circuits, are completely inhibited and thereby disabled by such pulsate interference, thus creating a substantial safety hazard. Furthermore, other types of EMI can be inadvertently modified through amplifier nonlinearities, filter circuits, protection diodes, or the like to create signals with repetition rates and spectral features within the range of normal cardiac activity, and these internally-generated signals will similarly inhibit a conventional demand pacer.

This problem is substantially overcome in the present invention by providing the second signal processing channel amplifier 31 with an enhanced high-frequency response with respect to the high-frequency response of first signal processing channel amplifier 21, as mentioned above. Thus, the bandpass of amplifier 31 might typically be from about 20 Hz up to at least about 300 Hz, to provide the desired high-frequency response. In this manner, the second signal processing channel is capable of detecting electromagnetic interference having spectral components falling within the passband of the first signal processing channel, and has relatively greater sensitivity than the first channel to the higher frequency spectral components that are present in most types of EMI.

Multivibrator 32, or an equivalent digital control function, is triggered by the output of amplifier 31 upon an EMI detection, and provides an output which is coupled to first signal processing channel 20 by gate control line 32a and rate control line 32b. Gate control line 32a is coupled to gate 23, and serves to open normally-closed switch 23a whenever multivibrator 32 is in the triggered state. When switch 23a is opened, the pulse-generating portion of the first signal processing channel is decoupled from the sensing portion thereof, so that multivibrator 24 cannot be inhibited by EMI pickup on electrode 40, even if the interference activates amplifier 21 and refractory interval generator 22. Retriggerable monostable multivibrator 32 will continue to provide a gate control signal on line 32a for so long as multivibrator 32 is triggered by a blocking signal from amplifier 31 in response to the detection of an EMI signal. As long as a control signal is present on gate control line 32a, switch 23a will remain open and the normal inhibit function of the first signal processing channel will be blocked. The duration of this blocking mode after each triggering of multivibrator 32 is controlled by providing an appropriate time constant for multivibrator 32.

During periods of EMI detection, when the pacer is operating in a fixed-rate mode, the first signal processing channel is rendered insensitive not only to EMI signals but to natural cardiac signals as well. For this reason, it may be desirable to operate astable multivibrator 24 at a higher rate than its normal fixed rate to minimize the possibility of competitive pacing, which may otherwise exist if the patient's natural heart rate exceeds the normal fixed rate. In order to switch astable multivibrator 24 to a higher fixed rate whenever EMI is detected, rate control line 32b couples the output of monostable multivibrator 32 to a rate control input of astable multivibrator 24. When a control signal is received at the rate control input of multivibrator 24, the astable multivibrator is switched to a second, higher fixed rate which may typically be in the range of from about 80 to 90 pulses per minute. A variety of circuit techniques for accomplishing this rate change, such as a simple switching circuit to alter either the resistive or capacitive element of the rate-determining time constant of multivibrator 24, will be within the purview of those skilled in the art. An alternate embodiment would entail modification of the decoded count in a digitally-controlled pacemaker. A reset control signal from the output of astable multivibrator 24 is coupled to monostable multivibrator 32 along reset line 24a to prevent the latter from being locked in its activated state due to pickup of artificial pacer pulses by EMI detection electrode 42.

When EMI pickup by electrode 42 ceases, monostable multivibrator 32 returns to its steady state, thereby removing the control signal from gate control line 32a and rate control line 32b. Accordingly, switch 23a will revert to its normally-closed state and the free-running rate of astable multivibrator 24 will be restored to its normal rate, thus returning the first signal processing channel to its demand configuration.

In FIG. 2, there is shown an alternate embodiment of the invention which switches to a rate-limited noise-synchronous mode upon detection of EMI. It should be noted that in FIG. 2, and in the subsequent FIGS., many system blocks are generally analogous to the system blocks shown in FIG. 1 and previously described in some detail. The last two digits of the reference numerals identifying such blocks in FIGS. 2–6 correspond to the reference numerals of FIG. 1. Thus, the pacer shown in FIG. 2 uses a pacing and sensing electrode 140 and an EMI sensing electrode 142, which connect respectively to a first signal processing channel 120 and a second signal processing channel 130 in a manner similar to that shown in FIG. 1. However, in FIG. 2, the output of refractory interval generator 122 is not gated, but rather is connected directly to resettable astable multivibrator 124. Thus, multivibrator 124 will be inhibited whenever EMI is detected on pacing and sensing electrode 140, and will cease to free-run at its fixed rate, thus inhibiting the generation of artificial cardiac stimulating pulses by output pulse generator 25. Accordingly, it is necessary for the second signal processing channel to serve as triggering channel for output pulse generator 125, to enable the pacer to provide stimulating pulses in the presence of interference. When EMI is detected by sensing electrode 142 and processed by bandpass amplifier 131, a detection signal is provided to system block 132, which is now shown as a nonretriggerable monostable multivibrator. Multivibrator 132 is triggered by a detection signal from amplifier 131 and generates a trigger signal on trigger line 132a in response thereto. Trigger signals on line 132a are fed to a trigger input of output pulse generator 125, to trigger the pulse generator and thus generate output pulses during periods when the first signal processing channel would otherwise be inhibited by the detection of interference. Monostable multivibrator 132 will be synchronously triggered by EMI detection signals from amplifier 131, but since multivibrator 132 is nonretriggerable, it cannot be triggered any faster than a predetermined maximum rate which is determined by the inherent time interval of the multivibrator circuit. This time interval is a selectable circuit parameter which may be chosen to achieve a desired maximum rate in the presence of EMI signals, such as 100 pulses per minute, thus ensuring that the pacer will operate in a safe rate-limited synchronous mode in the presence of normally inhibiting pulsate interference.

The essential function of the second signal processing channel in each of the embodiments shown in FIGS. 1 and 2 is therefore to prevent the first signal processing channel, which is basically a demand pacer, from being inhibited in the presence of detected EMI. In the embodiment of FIG. 1, this is accomplished essentially by disabling the inhibit function so that fixed-rate pulses will be generated during periods of EMI detection. In the embodiment of FIG. 2, on the other hand, the normal inhibit mode of the first signal processing channel is activated in the presence of an EMI detection, but a second, rate-limited triggering input is provided to override the inhibit mode and ensure that the output pulse generator will not be shut off by EMI. The result in each case is a demand-type pacing apparatus which is substantially safe in EMI fields, even when the interference is at rates which closely mimic normal cardiac activity.

Two further embodiments of a cardiac pacing apparatus having enhanced performance in EMI fields are shown in FIGS. 3 and 4. The configuration shown in FIGS. 3 and 4 correspond respectively to the fixed-rate output pacer of FIG. 1 and the rate-limited synchronous output of FIG. 2 in overall structure, but employ a single electrode for EMI detection as well as for pacing and sensing. In FIG. 3, for example, a single pacing, sensing and EMI detection electrode 240 provides inputs to both the first and second signal processing channels through input lines 240a and 240b, respectively. A similar single-electrode configuration is shown in the rate-limited synchronous output configuration of FIG. 4.

The use of a single electrode for EMI detection, as well as for pacing and sensing, results in a simplified electrode structure, and reduces the complexity of the electrode-pacer interface. However, the use of a common electrode also requires greater sophistication in the second signal processing channel, since this channel must now not only be sensitive to EMI signals, but also be rendered insensitive to natural cardiac signals appearing on its input line. In order to accomplish this dual function, the second channel bandpass amplifiers 231 and 331 of FIGS. 3 and 4 have a reduced low-frequency response with respect to the low-frequency response of first channel bandpass amplifiers 221 and 321, respectively, in addition to having an enhanced high-frequency response with respect to the first channel amplifiers as discussed above. Additionally, an input demodulator may be provided within the EMI filter amplifier to ensure detection of high level pulsed RF signals. Thus, each second channel amplifier may have a bandpass of from about 200 up to at least about 1000 Hz. In this manner, the second channel amplifiers will remain sensitive to the higher frequency spectral components characteristic of most types of EMI, while at the same time they will be rendered insensitive to natural cardiac signals, which do not contain substantial higher frequency spectral components and are also restricted in amplitude. Since the reduced low frequency response of amplifiers 231 and 331 below about 200 Hz renders the second signal processing channels of the embodiments of FIGS. 3 and 4 relatively insensitive to continuous interference in the passband at the first channel amplifiers, a conventional continuous interference rate discrimination circuit may be used in the first signal processing channels to prevent inhibition in the presence of 60 Hz of other continuous interference fields. The remaining portions of the cardiac pacers shown in FIGS. 3 and 4 correspond to the configurations shown in FIGS. 1 and 2, respectively, which are described above.

The pacer configurations shown in FIGS. 5 and 6 employ amplitude-based interference rejection input circuits in systems which otherwise correspond closely to those discussed above. Referring to FIG. 5, a single pacing, sensing and EMI detection electrode 440 is connected by a lead 440a to an amplifier 421a. The output of amplifier 421a is coupled to second signal processing channel 430 and to a second amplifier 421b in the first signal processing channel. A similar configuration is employed in the synchronous rate-limited pacer of FIG. 6. The purpose of this input configuration is to provide a dual-gain circuit having a higher gain for the first signal processing channel and a lower gain for the second channel. In the embodiment shown in FIG. 5, for example, the gain of the second signal processing channel 430 is the gain of amplifier 421a, while the gain of the first channel is the combined gain of amplifiers 421a and 421b. It will be apparent to those skilled in the art that various other amplifier configurations may be used to achieve this same result. For example, two parallel amplifiers having their inputs connected together and different gain functions might be used, or else a simple passive attenuator may be employed to provide a reduced gain function for the second signal processing channel.

The basic purpose of this dual-gain configuration is to provide the first signal processing channel with sufficient gain to detect even low-amplitude cardiac signals, down to about 1 millivolt, while providing the second signal processing channel with a sufficiently reduced gain to render it insensitive to even high-amplitude cardiac signals, up to about 40 millivolts. Thus, in FIG. 5, the combined gain function of amplifiers 421a and 421b would be approximately equivalent to the gain of amplifier 21 in FIG. 1, while the gain of amplifier 421a along is sufficiently below that level to render the second signal processing channel insensitive to substantially all natural cardiac signals. Since the range of normal cardiac signals is typically from about 1 millivolt to about 40 millivolts, the pacers of FIGS. 5 and 6 will function as conventional demand pacers in the presence of such signals, because the gain of their first amplifier stages, 421a and 521a respectively, is insufficient to activate their respective second signal processing channels. However, in the presence of EMI signals, which in many cases have substantially higher amplitude levels, the second signal processing channels 430 and 530 will switch the pacers to their safe fixed-rate or synchronous rate-limited modes.

Since the pacers of FIGS. 5 and 6 are dependent upon amplitude differentiation, rather than spectral differentiation, they may, unlike the embodiments of FIGS. 1-4, be inhibited by interference signals in the relatively narrow amplitude band corresponding to the amplitude range of normal cardiac signals. Nevertheless, the amplitude differentiation configurations of FIGS. 5 and 6 still offer a substantial improvement in EMI rejection as compared to conventional demand pacers, while requiring a minimum of extra complexity.

While the invention has been particularly shown and described with reference to certain preferred embodiments thereof, it will be understood by those skilled in the art that various changes in form and detail may be made without departing from the spirit and scope of the invention.

We claim:

1. An improved cardiac pacing apparatus of the type having first electrode means for sensing and pacing connectable to the heart; a first signal processing channel including means for generating artificial heart stimulating pulses at a predetermined rate and applying said pulses to said first electrode means, first bandpass amplifier means having an input connected to said first electrode means for detecting natural heart stimulating pulses, said artificial heart stimulating pulses and electromagnetic interference, and producing a detection signal having a rate in accordance therewith, and first control means, responsive to said detection signal and having an output operatively coupled to said means for generating artificial heart stimulating pulses, for continuously inhibiting the generation of said artificial pulses whenever the rate of said detection signal exceeds said predetermined rate; wherein the improvement comprises a second signal processing channel including:
 second bandpass amplifier means for detecting electromagnetic interference and producing a blocking signal in accordance therewith, said second bandpass amplifier means having an enhanced high frequency response with respect to the high frequency response of said first bandpass amplifier means to enhance the relative sensitivity of said second bandpass amplifier means to the higher frequency spectral components of said electromagnetic interference; and
 second control means, responsive to said blocking signal and having an output operatively coupled to said first control means, for preventing said first control means from inhibiting the generation of said artificial heart stimulating pulses whenever said blocking signal is produced, thereby causing the generation of artificial heart stimulating pulses at said predetermined rate whenever electromagnetic interference is detected by said second bandpass amplifier means.

2. An improved cardiac pacing apparatus as in claim 1, wherein said second bandpass amplifier means has a detecting input connected to said first electrode means in common with said first bandpass amplifier means, and wherein said second bandpass amplifier means has a reduced low frequency response with respect to said first bandpass amplifier means to render said second amplifier means substantially insensitive to natural cardiac signals.

3. An improved cardiac pacing apparatus as in claim 1, further comprising second electrode means remote from the heart for detecting electromagnetic interference and providing an input to said second bandpass amplifier means.

4. An improved cardiac pacing apparatus as in claim 1, wherein said means for generating artificial heart stimulating pulses at a predetermined rate comprises rate control means operatively coupled to the output of said second control means for selectably and momentarily switching said predetermined rate from a first, lower rate in the absence of an electromagnetic interference detection to a second, higher rate whenever said second control means is activated by a blocking signal from said second bandpass amplifier means for detecting electromagnetic interference.

5. An improved cardiac pacing apparatus of the type having a first electrode means for sensing and pacing connectable to the heart; a first signal processing channel including means for generating artificial heart stimulating pulses at a predetermined rate and applying said pulses to said first electrode means, first bandpass amplifier means having an input connected to said first electrode means for detecting natural heart stimulating pulses, said artificial heart stimulating pulses and electromagnetic interference, and producing a detection signal having a rate in accordance therewith, and first control means, responsive to said detection signal and having an output operatively coupled to said means for generating artificial heart stimulating pulses, for continuously inhibiting the generation of said artificial pulses whenever the rate of said detection signal exceeds said predetermined rate; wherein the improvement comprises a second signal processing channel including:
 second bandpass amplifier means for detecting electromagnetic interference and producing a second detection signal in accordance therewith, said second bandpass amplifier means having an enhanced high frequency response with respect to the high frequency response of said first bandpass amplifier means to enhance the relative sensitivity of said second bandpass amplifier means to the higher frequency spectral components of said electromagnetic interference; and
 second control means, responsive to said second detection signal and having a rate-limited output operatively coupled to said means for generating artificial heart stimulating pulses, for triggering said generating means at a rate in accordance with the rate of said second detection signal but at a rate no higher than a predetermined maximum rate, thereby causing the generation of rate-limited artificial heart stimulating pulses whenever electromagnetic interference is detected by said second bandpass amplifier means.

6. An improved cardiac pacing apparatus as in claim 5, wherein said second bandpass amplifier means has a detecting input connected to said first electrode means in common with said first bandpass means, and wherein second bandpass amplifier means has a reduced low frequency response with respect to said first bandpass amplifier means to render said second amplifier means substantially insensitive to natural cardiac signals.

7. An improved cardiac pacing apparatus as in claim 5, further comprising second electrode means remote from the heart for detecting electromagnetic interference and providing an input to said second bandpass amplifier means.

8. An improved cardiac pacing apparatus of the type having first electrode means for sensing and pacing connectable to the heart; a first signal processing channel including means for generating artificial heart stimulating pulses at a predetermined rate and applying said pulses to said first electrode means, first amplifier means having an input connected to said first electrode means for detecting natural heart stimulating pulses, said artificial heart stimulating pulses and electromagnetic interference, and producing a detection signal having a rate in accordance therewith, and first control means, responsive to said detection signal and having an output operatively coupled to said means for generating artificial heart stimulating pulses, for continuously inhibiting the generation of said artificial pulses whenever the rate of said detection signal exceeds said predetermined rate; wherein the improvement comprises a second signal processing channel including:

- second amplifier means, for detecting electromagnetic interference having an amplitude level above that of natural heart stimulating pulses and producing a blocking signal in accordance therewith, the gain of said second amplifier means being reduced with respect to the gain of said first amplifier means sufficiently to render said second signal processing channel insensitive to natural heart stimulating pulses; and
- second control means, responsive to said blocking signal and having an output operatively coupled to said first control means, for preventing said first control means from inhibiting the generation of said artificial heart stimulating pulses whenever said blocking signal is produced, thereby causing the generation of artificial heart stimulating pulses at said predetermined rate whenever electromagnetic interference having an amplitude level above that of natural heart stimulating pulses is detected by said second amplifier means.

9. An improved cardiac pacing apparatus of the type having first electrode means for sensing and pacing connectable to the heart; a first signal processing channel including means for generating artificial heart stimulating pulses at a predetermined rate and applying said pulses to said first electrode means, first amplifier means having an input connected to said first electrode means for detecting natural heart stimulating pulses, said artificial heart stimulating pulses and electromagnetic interference, and producing a detection signal having a rate in accordance therewith, and first control means, responsive to said detection signal and having an output operatively coupled to said means generating artificial heart stimulating pulses, for continuously inhibiting the generation of said artificial pulses whenever the rate of said detection signal exceeds said predetermined rate; wherein the improvement comprises a second signal processing channel including:

- second amplifier means for detecting electromagnetic interference having an amplitude level above that of natural heart stimulating pulses and producing a second detection signal in accordance therewith, the gain of said second amplifier means being reduced with respect to the gain of said first amplifier means sufficiently to render said second signal processing channel insensitive to natural heart stimulating pulses; and
- second control means, responsive to said second detection signal and having a rate-limited output operatively coupled to said means for generating artificial heart stimulating pulses, for triggering said generating means at a rate in accordance with the rate of said second detection signal but at a rate no higher than a predetermined maximum rate, thereby causing the generation of rate-limited artificial heart stimulating pulses whenever electromagnetic interference having an amplitude level above that of natural heart stimulating pulses is detected by said second amplifier means.

* * * * *

UNITED STATES PATENT AND TRADEMARK OFFICE
CERTIFICATE OF CORRECTION

PATENT NO. : 4,091,818
DATED : May 30, 1978
INVENTOR(S) : Robert R. Brownlee and G. Frank O. Tyers It is certified that error appears in the above-identified patent and that said Letters Patent are hereby corrected as shown below:

Col. 3, line 37, after "dual-electrode," insert --rate-limited--;

Col. 6, line 65, "25" should read --125--;
line 67, after "as" insert --a--;

Col. 7, line 47, after "output" insert --pacer--;

Col. 8, line 23, "of" (second occurrence) should read --or--;

Col. 10, line 64, (Claim 6, line 4) after "bandpass" insert --amplifier--.

Signed and Sealed this

Twenty-fourth Day of October 1978

[SEAL]

Attest:

RUTH C. MASON
Attesting Officer

DONALD W. BANNER
Commissioner of Patents and Trademarks